United States Patent [19]

Taylor et al.

[11] Patent Number: 4,883,799

[45] Date of Patent: Nov. 28, 1989

[54] N-(4-(1-HYDROXY-3-(5,6,7,8-TETRAHYDROPYRIDO(2,3,-D)-PYRIMIDIN-6-YL)PROP-2-YL)BENZOYL)GLUTAMIC ACID DERIVATIVES

[75] Inventors: Edward C. Taylor; Cheol-min Yoon, both of Princeton, N.J.

[73] Assignee: The Trustees of Princeton University, Princeton, N.J.

[21] Appl. No.: 213,275

[22] Filed: Jun. 29, 1988

[51] Int. Cl.$^4$ .................. A61K 31/505; C07D 425/08
[52] U.S. Cl. ..................................... 514/258; 544/279
[58] Field of Search ........................ 544/279; 514/258

[56] References Cited

U.S. PATENT DOCUMENTS 4,684,653  8/1987  Taylor et al. ...................... 544/279

Primary Examiner—Muykund I. Sham
Assistant Examiner—Carol Lynn Cseh
Attorney, Agent, or Firm—Mathews, Woodbridge, Goebel, Pugh & Collins

[57] ABSTRACT

N-[4-{1-Hydroxy-3-(2-amino-4-hydroxy-5,6,7,8-tetrahydropyrido[2,3-d]pyrimidin-6-yl)prop-2-yl )benzoyl]-glutamic acid, it salts, and derivatives thereof, have an inhibitory effect on one or more enzymes which utilize folic acid and can be used, alone or in combination, to inhibit the growth of those neoplasms which otherwise depend upon the enzymes so inhibited. The compounds can be prepared through catalytic hydrogenation of a protected derivative of N-[4-{1-hydroxy-3-(2-amino-4-hydroxy-pyrido[2,3-d]pyrimidin-6-yl)prop-2-en-2-yl)benzoyl]glutamic acid and removal of the protecting groups.

6 Claims, No Drawings

N-(4-(1-HYDROXY-3-(5,6,7,8-TETRAHYDROPYRIDO(2,3,-D)-PYRIMIDIN-6-YL)PROP-2-YL)BENZOYL)GLUTAMIC ACID DERIVATIVES

The present invention pertains to the individual diastereomers and to the diastereomeric mixture of glutamic acid derivatives of the formula:

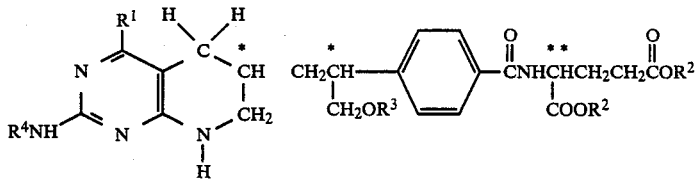

in which:
R¹ is —OH or —NH₂;
R² is hydrogen or a carboxy protecting group;
R³ is hydrogen or a hydroxy protecting group;
R⁴ is hydrogen or an amino protecting group;
the configuration about the carbon atoms designated C* is (R) or (S) and the configuration about the carbon atom designated C** is (S); and
the pharmaceutically acceptable salts thereof.

The compounds of Formula I have an inhibitory effect on one or more enzymes which utilize folic acid, and in particular metabolic derivatives of folic acid, as a substrate. The compounds thus can be used, alone or in combination, to inhibit the growth of those neoplasms which otherwise depend upon the enzymes so inhibited.

The invention also pertains to the pharmaceutically acceptable salts of the compounds of Formula IA and IB, to processes for the preparation of these compounds and their salts, to a method of combatting neoplastic growth in a mammal, and to pharmaceutical compositions containing these compounds or their salts.

The protecting groups designated by R², R³, and R⁴ and utilized herein denote groups which generally are not found in the final therapeutic compounds but which are intentionally introduced during a portion of the synthesis to protect a group which otherwise might react in the course of chemical manipulations, thereafter being removed at a later stage of the synthesis. Since compounds bearing such protecting groups thus are of importance primarily as chemical intermediates (although some derivatives also exhibit biological activity), their precise structure is not critical. Numerous reactions for the formation and removal of such protecting groups are described in a number of standard works including, for example, "Protective Groups in Organic Chemistry", Plenum Press, London and New York, 1973; Greene, Th. W. "Protective Groups in Organic Synthesis", Wiley, N. Y., 1981; "The Peptides", Vol. I, Schrooder and Lubke, Academic Press, London and New York, 1965; "Methoden der organischen Chemie", Houben-Weyl, 4th Edition, Vol. 15/I, Georg Thieme Verlag, Stuttgart 1974.

A carboxy group can be protected as an ester group which is selectively removable under sufficiently mild conditions not to disrupt the desired structure of the molecule, especially a lower alkyl ester such as methyl or ethyl and particularly one which is branched at the 1-position such as t.-butyl; and such lower alkyl ester substituted in the 1- or 2-position with (i) lower alkoxy, such as for example, methoxymethyl, 1-methoxyethyl, and ethoxymethyl, (ii) lower alkylthio, such as for example methylthiomethyl and 1-ethylthioethyl; (iii) halogen, such as 2,2,2-trichloroethyl, 2-bromoethyl, and 2-iodoethoxycarbonyl; (iv) one or two phenyl groups each of which can be unsubstituted or mono-, di- or tri-substituted with, for example lower alkyl such as tert.-butyl, lower alkoxy such as methoxy, hydroxy, halo such as chloro, and nitro, such as for example, benzyl, 4-nitrobenzyl, diphenylmethyl, di-(4-methoxyphenyl)methyl; or (v) aroyl, such as phenacyl. A carboxy group can also be protected in the form of an organic silyl group such as tri-lower alkylsilyl, as for example trimethylsilyloxycarbonyl.

Hydroxy groups can be protected for example through the formation of acetals and ketals, as for example though formation of tetrahydropyr-2-yloxy (THP) derivative.

Amino groups can be protected as an amide utilizing an acyl group which is selectively removable under mild conditions, especially formyl, a lower alkanoyl group which is branched in the position adjacent to the carbonyl group, particularly tertiary alkanoyl such as pivaloyl, or a lower alkanoyl group which is substituted in the position adjacent to the carbonyl group, as for example trifluoroacetyl.

The preferred compounds are those wherein R¹ is OH and each of R², R³ and R⁴ is hydrogen. Three chiral centers are present, designated in Formula I as C* and C**. The configuration about the two carbon atoms designated C* can be either (R) or (S) while that about the carbon atom designated C** will be (S). Thus preferred species include (R,R,S) N-4-{1-hydroxy-3-(2-amino-4-hydroxy-5,6,7,8-tetrahydropyrido[2,3-d]pyrimidin-6-yl)prop-2-yl}benzoyl]glutamic acid, (S,R,S) N-[4-{1-hydroxy-3-(2-amino-4-hydroxy-5,6,7,8-tetrahydropyrido[2,3-d]pyrimidin-6-yl)prop-2-yl}benzoyl]glutamic acid, (R,S,S) N-[4-{1-hydroxy-3-(2-amino-4-hydroxy-5,6,7,8-tetrahydropyrido[2,3-d]pyrimidin-6-yl)prop-2-yl}benzoyl]glutamic acid, and (S,S,S) N-[4-{1-hydroxy-3-(2-amino-4-hydroxy-5,6,7,8-tetrahydropyrido[2,3-d]pyrimidin-6-yl)prop-2-yl}benzoyl]glutamic acid.

The compounds of the present invention often can be employed advantageously in the form of a pharmaceutically acceptable salt. Such forms, including hydrates thereof, are often crystalline and advantageous for forming solutions or formulating pharmaceutical compositions. Pharmaceutically acceptable salts with bases include those formed from the alkali metals, alkaline earth metals, non-toxic metals, ammonium, and mono-, di- and trisubstituted amines, such as for example the sodium, potassium, lithium, calcium, magnesium, aluminum, zinc, ammonium, trimethylammonium, triethanolammonium, pyridinium, and substituted pyridinium salts. The mono and disodium salts, particularly the disodium salt, are advantageous.

The compounds of this invention can be prepared through catalytic hydrogenation of a compound of the formula:

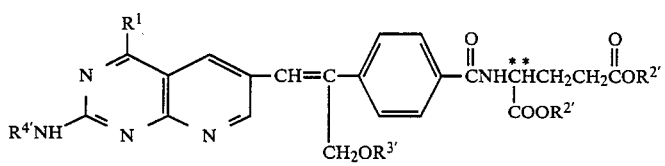 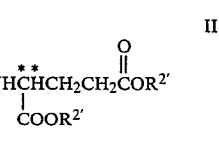

in which:

R$^1$ is as herein defined;

R$^{2'}$ is a carboxy protecting group; and

R$^{3'}$ is a hydroxy protecting group; and

R$^{4'}$ is an amino protecting group.

Suitable hydrogenation catalysts include noble metals and noble metal oxides such as palladium or platinum oxide, rhodium oxide, and the foregoing on a support such as carbon or calcium oxide.

There is obtained a mixture of diastereomers of Formula I which R$^{2'}$ is a carboxy protecting group, R$^{3'}$ is a hydroxy protecting group, and R$^{4'}$ is an amino protecting group. The hydroxy protecting group R$^{3'}$ then can be removed through acidic hydrolysis, and the R$^{2'}$ and R$^{4'}$ protecting groups through acidic or basic hydrolysis, as for example with sodium hydroxide, to yield the compounds of Formula I in which each of R$^2$, R$^3$ and R$^4$ is hydrogen.

Compounds of Formula II can be prepared by allowing an unsaturated compound of the formula:

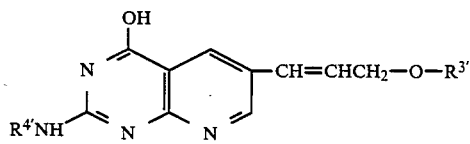

in which R$^{3'}$ and R$^{4'}$ are as herein defined, and the configuration about the olefinic bond is cis, to react with compound of the formula:

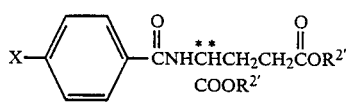

in which X is bromo or iodo and R$^{2'}$ is as herein defined, in the presence of a palladium/trisubstituted phosphine catalyst of the type described by Sakamoto, *Synthesis*, 1983, 312 et seq.

There thus is obtained a compound of Formula II in which R$^1$ is —OH. When a compound in which R$^1$ is —NH$_2$ is desired, this product can be treated with 1,2,4-triazole and (4-chlorophenyl)dichlorophosphate and the product of this reaction then treated with concentrated ammonia in the manner described by Adamiak et al., *Chemica Scripta*, 1986, 26, 3-6 and references cited therein.

The intermediates of Formula III can be prepared by first allowing a compound of the formula:

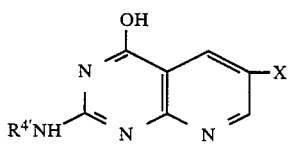

in which R$^{4'}$ and X are as herein defined, to react with compound of the formula:

$$HC\equiv CCH_2-O-R^{3'} \qquad VI$$

in which R$^{3'}$ is as herein defined, again using a palladium/trisubstituted phosphine catalyst of the type described by Sakamoto, *Synthesis*, 1983, 312 et seq.

Thus obtained is an acetylenic compound of the formula:

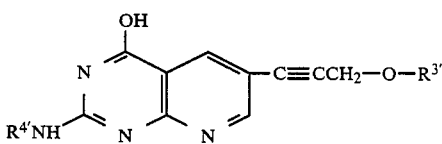

Selective catalytic hydrogenation, as with palladium on barium sulfate, then yields the desired intermediate of Formula III.

Compounds of Formula IV are prepared by coupling a halobenzoic acid derivative with a protected glutamic acid derivative in the manner generally described in PCT application WO 86/05181, namely through conventional condensation techniques for forming peptide bonds, such as activation of the carboxy group through formation of a mixed anhydride, treatment with DCC, or use of diphenyl-chlorophosphonate.

The mixture of the individual diastereomers depicted by Formula I can be used therapeutically as such or can be separated mechanically as by chromatography. Alternatively, the individual diastereomers can be separated by forming diastereomeric salts with a chiral acid such as the individual enantiomers of 10-camphorsulfonic acid, camphoric acid, alpha-bromocamphoric acid, methoxyacetic acid, tartaric acid, diacetyltartaric acid, malic acid, pyrrolidone-5-carboxylic acid, and the like, and then freeing the individual diastereomeric bases, optionally repeating the process, so as obtain each substantially free of the others; i.e., in a form having an optical purity of >95%. This separation can be effected before or after removal of any protecting groups.

As noted, the compounds of this invention have an effect on one or more enzymes which utilize folic acid, and in particular metabolic derivatives of folic acid, as a substrate. The compounds can be used, under the supervision of qualified professionals, to inhibit the growth of neoplasms including choriocarcinoma, leukemia, adenocarcinoma of the female breast, epidermid cancers of the head and neck, squamous or small-cell lung cancer, and various lymphosarcomas. The compounds can also be used to treat mycosis fungoides and psoriasis.

The compounds can be administered orally but preferably are administered parenterally, alone or in combination with other therapeutic agents including other anti-neoplastic agents, steroids, etc., to a mammal suffering from neoplasm and in need of treatment. Parenteral routes of administration include intramuscular, intrathecal, intravenous and intra-arterial. Dosage regimens must be titrated to the particular neoplasm, the condition of the patient, and the response but generally doses will be from about 10 to about 100 mg/day for 5-10 days or single daily administration of 250-500 mg, repeated periodically; e.g. every 14 days. While having a low toxicity as compared to other antimetabolites now in use, a toxic response often can be eliminated by either or both of reducing the daily dosage or administering the compound on alternative days or at longer intervals such as every three days. Oral dosage forms include tablets and capsules containing from 1-10 mg of drug per unit dosage. Isotonic saline solutions containing 20-100 mg/ml can be used for parenteral administration.

The following examples will serve to further illustrate the invention. In the NMR data, "s" denotes singlet, "d" denotes doublet, "t" denotes triplet, "q" denotes quartet, "m" denotes multiplet, and "br" denotes a broad peak.

EXAMPLE 1

2-Pivaloylamino-4-hydroxy-6-(3-tetrahydropyr-2-yloxyprop-1-yn-1-yl)-pyrido[2,3-d]pyrimidine A mixture of 14.61 g (46 mmol) of 2-pivaloylamino-4-hydroxy-6-bromopyrido[2,3-d]pyrimidine, 7.6 g (1.2 eqv.) of 2-(2-propynyloxy)-tetrahydropyran, 798 mg (10%) of palladium chloride, 2.36 g (20%) of triphenyl phosphine, 428 mg (5%) of cuprous iodide, 45 ml of triethyl amine and 700 ml of acetonitrile was heated at reflux under nitrogen for 12 hours. There then were added to the hot reaction mixture 3.2 g of 2-(2-propynyloxy)-tetrahydropyran and reflux was continued for an additional 12 hours. After heating for a total of 24 hours under reflux, the solvent was removed under reduced pressure, and the residue filtered through silica gel using 2% methanol in methylene chloride. This filtrate was concentrated and chromatographed on silica gel eluting with 20:1 ethyl acetate:hexane mixture to give 10.94 g (63.2%) of 2-pivaloylamino-4-hdyroxy-6-(3-tetrahydropyr-2-yloxyprop-1-yn-1-yl)-pyrido[2,3-d]pyrimidine which was further purified by recrystallization with ethyl acetate. m.p. 212°-214° C. Analysis Calculated for $C_{20}H_{24}N_4O_4$: C, 62.48; H, 6.29; N, 14.58. Found: C, 62.53; H, 6.46; N, 14.47. NMR (CDCL$_3$), delta, 1.35 (s, 9H), 1.56-1.90 (m, 6H), 3.57-3.63 (m, 1H), 3.87-3.95 (m, 1H), 4.50 (d, 1H, J=16 Hz), 4.57 (d, 1H, J=16 Hz), 8.35 (brs, NH), 8.55 (d, 1H, J=2 Hz), 8.90 (d, 1H, J=2 Hz), 12.09 (brs, NH).

EXAMPLE 2

2-Pivaloylamino-4-hydroxy-6-(3-tetrahydropyr-2-yloxyprop-1-en-1-yl)-pyrido[2,3-d]pyrimidine A mixture of 2 g (5.2 mm) of 2-pivaloylamino-4-hydroxy-6-(3-tetrahydropyr-2-yloxyprop-1-yn-1-yl)-pyrido[2,3-d]pyrimidine, 40 ml of methanol, 20 ml of chloroform, 40 mg of 5% palladium on barium sulfate, and 40 mg of synthetic quinoline was stirred under 1 atm hydrogen pressure for 40 min. The solvent then was removed by evaporation and the residue diluted with methylene chloride. The methylene chloride solution was filtered through silica gel with 2% methanol in methylene chloride to remove catalyst and the filtrate then concentrated to give an oil which upon adding ether yielded 1.74 g (86.6%) of 2-pivaloylamino-4-hydroxy-6-(3-tetrahydropyr-2-yloxyprop-1-en-1-yl)-pyrido[2,3-d]pyrimidine as yellow crystals which was further purified through column chromatography eluting with ethyl acetate and recrystallization using ethyl acetate. mp 166°-167° C. Analysis: Calculated for $C_{20}H_{26}O_4N_4$: C, 62.16; H, 6.78; N, 14.50. Found: C, 62.30; H, 6.88; N, 14.74. NMR (CDCl$_3$), delta, 1.35 (s, 9H), 1.54-1.88 (m, 6H), 3.51-3.58 (m, 1H), 3.85-3.93 (m, 1H), 4.26-4.33 (m, 1H), 4.51-4.57 (m, 1H), 4.70 (t, 1H, J=3.4 Hz), 6.07-6.15 (m, 1H), 6.62 (d, 1H, J=12.1 Hz), 8.35 (brs, NH), 8.37 (d, 1H, J=2.5 Hz), 8.79 (d, 1H, J=2.5 Hz), 12.7 (brs, NH).

EXAMPLE 3

Diethyl N-[4-{1-(Tetrahydropyr-2-yloxy)-3-(2-pivaloylamino-4-hydroxypyrido[2,3-d]pyrimidin-6-yl)prop-2-en-2-yl}benzoyl]glutamate A mixture containing 3.48 g (9 mm) of 2-pivaloylamino-4-hydroxy-6-(3-tetrahydropyr-2-yloxyprop-1-en-1-yl)-pyrido[2,3-d]pyrimidine, 3.12 g, (1.2 equiv.) of diethyl N-(4-iodobenzoyl)glutamate, 546 mg (20%) of tris(2-methylphenyl)phosphine, 201 mg (10%) of palladium acetate and 85.5 mg (5%) of cuprous iodide in 15 ml of triethylamine and 240 ml of acetonitrile was heated at reflux under nitrogen. After 12 hours., 1.17 g of diethyl N-(4-iodobenzoyl)glutamate was added and the reaction mixture was heated at reflux under nitrogen for an additional 12 hours. The reaction mixture then was concentrated under reduced pressure and the residue was chromatographed on silica gel, eluting with 20:1 ethyl acetate:hexane. (Recovered starting material can be recycled through the foregoing procedure.) The concentrated material was dissolved in 1:5 ethyl acetate:ether and this solution was refrigerated for 15 hours. The solid which formed was collected by filtration, washed with cold ethyl acetate and dried to yield diethyl N-[4-{1-(tetrahydropyr-2-yloxy)-3-(2-pivaloylamino-4-hydroxypyrido[2,3-d]pyrimidin-6-yl)prop-2-en-2-yl}benzoyl]glutamate. mp. 273°-275° C. Analysis calculated for $C_{36}H_{45}N_4O_9$; C, 62.50; H, 6.56; N, 10.12. Found: C, 62.21; H, 6.34; N, 9.83. NMR (CDCL$_3$), delta, 1.24 (t, 3H, J=7 Hz), 1.32 (t 3H, J=7 Hz), 1.32 (s, 9H), 1.53-1.87 (m, 6H), 2.11-2.22 (m, 1H), 2.29-2.41 (m 1H), 2.42-2.58 (m, 2H), 3.53-3.59 (m, 1H), 3.80-3.88 (m, 1H), 4.13 (q, 2H, J=7 Hz), 4.25 (q, 2H, J=7 Hz), 4.33 (d, 1H, J=14 Hz), 4.62 (d, 1H, J=14 Hz), 4.75-4.83 (m, 2H), 6.84 (s, 1H), 7.12 (brs, 1H, NH, J=7 Hz), 7.31 (d, 2H, J=8.1 Hz), 7.79 (d, 2H, J=8.1 Hz), 8.13 (d, 1H, J=1.6 Hz), 8.34 (brs, NH), 8.42 (d, 1H, J=1.6 Hz), 11.99 (brs, NH).

EXAMPLE 4

Diethyl N-[4-{1-(Tetrahydropyr-2-yloxy)-3-(2-pivaloylamino-4-hydroxy-5,6,7,8-tetrahydropyrido[2,3-d]pyrimidin-6-yl)prop-2-yl}benzoyl]glutamate A solution of 1.16 g (1.68 mm) of diethyl N-[4-{1-(tetrahydropyr-2-yloxy)-3-(2-pivaloylamino-4-hydroxypyrido[2,3-d]pyrimidin-6-yl)prop-2-en-2-yl}benzoyl]-glutamate and 174 mg (20%) of amorphous platinum (IV) oxide in 150 ml of glacial acetic acid was hydrogenated for 10 hours at 50 psi. The reaction mixture was diluted with 50 ml of methanol and filtered through Celite. The filtrate was concentrated and diluted with ethyl acetate. The solid which formed after cooling for 15 hour was collected by filtration, washed with cold ethyl acetate and dried to give 700 mg (68%) of diethyl N-[4-{1-(tetrahydropyr-2-yloxy)-3-(2-pivaloylamino-4- hydroxy-5,6,7,8-tetrahydropyrido[2,3-d]pyrimidin-6-yl)prop-2-yl}benzoyl]glutamate. mp 183°–186° C. Analysis calculated for $C_{36}H_{51}O_9N_5$: C, 61.95; H, 7.37; N, 10.04. Found: C, 62.00; H, 7.17; N, 9.83. NMR ($CDCL_3$), delta, 1.23 (t, 3H, J=7 Hz), 1.26 (s, 9H), 1.32 (t, 3H, J=7 Hz), 2.26–2.82 (m, 9H), 2.06–2.12 (m, 2H), 2.26–2.38 (m, 1H), 2.43–2.58 (m, 2H), 2.62–2.83 (m, 1H), 2.84–3.10 (m, 2H) 3.12–3.21 and 2.32–3.40 (m, m, 1H), 3.41–3.52 (m, 2H), 3.68–3.92 (m, 2H), 4.13 (q, 2H, J=7 Hz), 4.25 (q, 2H, J=7 Hz), 4.44–4.63 (m, 2H, CH, NH), 4.78–4.84 (m, 1H) 7.02 (brd, 1H, NH, J=7.1 Hz), 7.29 (brs, NH), 7.31–7.37 (m, 2H), 7.75–7.78 (m, 2H), 11.20 (brs, NH).

EXAMPLE 5

Diethyl
N-[4-{1-Hydroxy-3-(2-pivaloylamino-4-hydroxy-5,6,7,8-tetrahydropyrido[2,3-d]pyrimidin-6-yl)prop-2-yl}benzoyl]glutamate The solution of 942 mg (1.35 mm) of diethyl N-[4-{1-(tetrahydropyr-2-yloxy)-3-(2-pivaloylamino-4-hydroxy-5,6,7,8-tetrahydropyrido[2,3-d]pyrimidin-6-yl)prop-2-yl}benzoyl]glutamate in 40 ml of 0.1N methanolic hydrogen chloride was stirred at ambient temperatures for 2 hours. The reaction mixture was neutralized with a solution of 205 mg of sodium carbonate in 10 ml of water and most of methanol was removed by evaporation under reduced pressure. One hundred milliliters of methylene chloride were added the solution was washed twice with 20 ml of water, dried over anhydrous magnesium sulfate, and concentrated. The residue was triturated with 1:2 ethyl acetate and ether, filtered, and dried to give 810 mg (98%) of diethyl N-[4-{1-hydroxy-3-(2-pivaloylamino-4-hydroxy-5,6,7,8-tetrahydropyrido[2,3-d]pyrimidin-6-yl)prop-2-yl}benzoyl]glutamate. mp 133°–135° C. Analysis calculated for $C_{31}H_{43}N_5O_8$: C, 60.67; H, 7.06; N, 11.41. Found: C, 60.42; H, 7.09; N, 11.34. NMR ($CDCl_3$), delta, 1.22 (t, 3H, J=7 Hz), 1.26 (s, 9H), 1.30 (t, 3H, J=7 Hz), 1.78–1.87 (m, 3H), 2.01–2.23 (m, 3H), 2.23–2.36 (m, 1H), 2.38–2.54 (m, 2H), 2.59–2.69) (m, 1H), 2.83–3.12 (m, 2H), 3.14–3.18 and 3.28–3.32 (m, m, 1H), 3.72–3.78 (m, 2H), 4.12 (q, 2H, J=7 Hz), 4.23 (q, 2H, J=7 Hz), 4.74–4.84 (m, 2H, CH, NH), 7.24 (d, NH, J=7 Hz), 7.26–7.30 (m, 1H), 7.72–7.76 (m, 1H), 8.09 (brs, NH), 11.23 (brs, NH).

EXAMPLE 6

N-[4-{1-Hydroxy-3-(2-amino-4-hydroxy-5,6,7,8-tetrahydropyrido[2,3-d]pyrimidin-6-yl)prop-2-yl}benzoyl]glutamic Acid A solution of 300 mg (0.49 mm) of diethyl N-[4-{1-hydroxy-3-(2-pivaloylamino-4-hydroxy-5,6,7,8-tetrahydropyrido[2,3-d]pyrimidin-6-yl)prop-2-yl}benzoyl]glutamate in 9 ml of 1N aqueous sodium hydroxide was stirred under nitrogen at ambient temperature for 72 hours. The reaction mixture was rendered slightly acidic (pH=~4) with 1N hydrochloric acid and filtered. The solid thus collected was washed with water (5 ml) and cold ethanol (5 ml) and dried to give 180 mg (78%) of N-[4-{1-hydroxy-3-(2-amino-4-hydroxy-5,6,7,8-tetrahydropyrido[2,3-d]pyrimidin-6-yl)prop-2-yl}benzoyl]glutamic acid. mp 275° C. (dec.). Analysis calculated for $C_{22}H_{27}N_5O_7 \cdot 0.5H_2O$: C, 54.76; H, 5.80; N, 14.51. Found: C, 54.96; H, 5.88; N, 14.27. NMR ($DMSOd_6$, $CF_3COOD$), delta, 1.35–1.42 (m, 1H), 1.58–1.71 (m, 2H), 1.73–1.85 (m, 1H), 1.86–2.01 (m, 1H), 2.02–2.13 (m, 1H), 2.31 (t, 2H, J=7 Hz), 2.39–2.52 (m, 1H), 2.74–2.89 (m, 2H), 3.08–3.14 and 3.24–3.30 (m, m, 1H), 3.47 (d, 2H, J=3.7 Hz), 4.37 (dd, 1H, J=19.4 Hz, J=4.7 Hz), 7.27–7.30 (m, 2H), 7.78 (d, 2H, J=7.7 Hz).

What is claimed is:

1. A compound selected from the group consisting of a glutamic acid derivative having the formula:

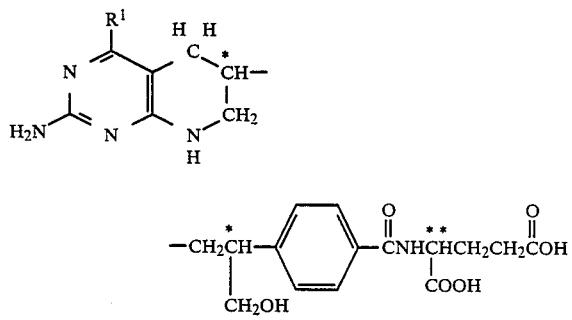

in which
the configuration about the carbon atoms designated C* is (R) or (S), and the configuration about the carbon atom designated C** is (S); and
the pharmaceutically acceptable salts thereof.

2. A compound according to claim 1 wherein said glutamic acid derivative is N-[4-{1-hydroxy-3-(2-amino-4-hydroxy-5,6,7,8-tetrahydropyrido[2,3-d]pyrimidin-6-yl)prop-2-yl}benzoyl]glutamic acid.

3. The disodium salt of the glutamic acid derivative of claim 2.

4. The method of inhibiting neoplastic growth in a mammal which growth is dependent on folic acid or a metabolic derivative of folic acid as a substrate, which comprises administering to the mammal in a single or multiple dose regimen an effective amount of a compound according to claim 1.

5. A pharmaceutical composition for inhibiting neoplastic growth in a mammal which growth is dependent on folic acid or a metabolic derivative of folic acid as a substrate, which comprises an amount of a compound according to claim 1 which upon administration to the mammal in a single or multiple dose regimen is effective to inhibit said growth, in combination with a pharmaceutically acceptable carrier.

6. A compound selected from the group consisting of a glutamic acid derivative having the formula:

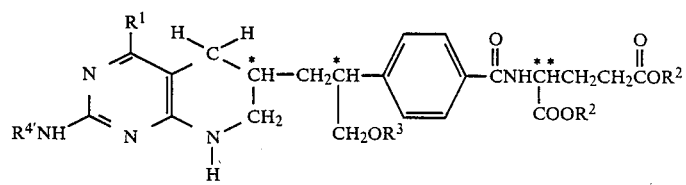

in which:

$R^1$ is —OH or —NH$_2$;

$R^2$ is hydrogen or a carboxy protecting group selected from the group consisting of (a) a straight or branched lower alkyl ester which is unsubstituted or substituted in the 1- or 2-position with (i) lower alkoxy, (ii) lower alkylthio, (iii) halogen, (iv) phenyl which is unsubstituted or mono-, di- or tri-substituted with lower alkyl, lower alkoxy, hydroxy, halo, or nitro, or (v) aroyl, or (b) a silyl group;

$R^3$ is hydrogen or a hydroxy protecting group selected from the group consisting of an acetal and a ketal;

$R^4$ is hydrogen or an unsubstituted or substituted acyl amino protecting group;

at least one of $R^2$, $R^3$, and $R^4$ being other than hydrogen;

the configuration about the carbon atoms designated C* is (R) or (S), and the configuration about the carbon atom designated C** is (S); and the pharmaceutically acceptable salts thereof.

* * * * *